US012576229B2

(12) United States Patent
Moir et al.

(10) Patent No.: US 12,576,229 B2
(45) Date of Patent: Mar. 17, 2026

(54) BEARING SLEEVE FOR BLOWER

(71) Applicant: RESMED MOTOR TECHNOLOGIES INC., Chatsworth, CA (US)

(72) Inventors: Michael Bruce Moir, Newbury Park, CA (US); Christopher Scott Edwards, Canoga Park, CA (US)

(73) Assignee: RESMED MOTOR TECHNOLOGIES INC., Chatsworth, CA (US)

( * ) Notice: Subject to any disclaimer, the term of this patent is extended or adjusted under 35 U.S.C. 154(b) by 820 days.

(21) Appl. No.: 17/908,967

(22) PCT Filed: Mar. 3, 2021

(86) PCT No.: PCT/US2021/020656
§ 371 (c)(1),
(2) Date: Sep. 2, 2022

(87) PCT Pub. No.: WO2021/178527
PCT Pub. Date: Sep. 10, 2021

(65) Prior Publication Data
US 2023/0100486 A1 Mar. 30, 2023

Related U.S. Application Data

(60) Provisional application No. 62/984,515, filed on Mar. 3, 2020.

(51) Int. Cl.
*A61M 16/06* (2006.01)
*A61M 16/00* (2006.01)
(Continued)

(52) U.S. Cl.
CPC ........ *A61M 16/06* (2013.01); *A61M 16/0057* (2013.01); *F04D 29/056* (2013.01); *F04D 29/668* (2013.01); *F05D 2240/50* (2013.01)

(58) Field of Classification Search
CPC .......... A61M 16/0066; A61M 16/0069; A61M 16/021; A61M 16/0605; A61M 16/0633;
(Continued)

(56) References Cited

U.S. PATENT DOCUMENTS 3,451,736 A 6/1969 Riccio
3,568,962 A 3/1971 Janssen
(Continued)

FOREIGN PATENT DOCUMENTS

CN 101553667 A 10/2009
CN 103429289 A 12/2013
(Continued)

OTHER PUBLICATIONS

Extended European Search Report mailed Feb. 19, 2024 in European Application No. 21765107.4, 10 pages.
(Continued)

*Primary Examiner* — Annette Dixon
(74) *Attorney, Agent, or Firm* — Nixon & Vanderhye P.C.

(57) ABSTRACT
A blower includes a rotor, a motor adapted to drive the rotor, at least one bearing to rotatably support the rotor, a stationary component, and a bearing sleeve provided to the stationary component. The bearing sleeve is structured and arranged to support and retain the bearing to the stationary component. The bearing sleeve comprises an elastomeric material, and the bearing sleeve comprises one or more bumps or ribs configured to engage along an outer race of the bearing.

9 Claims, 17 Drawing Sheets

(51) Int. Cl.
    *F04D 29/056*     (2006.01)
    *F04D 29/66*     (2006.01)

(58) Field of Classification Search
    CPC .............. A61M 16/0683; A61M 16/10; A61M 2016/0027; A61M 2016/0039; A61M 2205/0216; A61M 2205/07; A61M 2205/10; A61M 2205/3331; A61M 2205/42; A61M 2205/8206; A61M 2209/088; F04D 17/122; F04D 17/16; F04D 17/164; F04D 19/04; F04D 25/0693; F04D 29/023; F04D 29/0563; F04D 29/058; F04D 29/059; F04D 29/281; F04D 29/4206; F04D 29/4226; F04D 29/4233; F04D 29/441; F04D 29/626; F04D 29/665; F04D 29/668; F05D 2300/43; F16B 2/08; F16C 19/06; F16C 2226/30; F16C 2360/45; F16C 27/04; F16C 27/066; F16C 35/067; F16C 35/077; F16H 55/48; H02K 5/161; Y10T 29/4984; Y10T 29/4987

See application file for complete search history.

(56)            References Cited

U.S. PATENT DOCUMENTS

| | | | |
|---|---|---|---|
| 4,302,927 A | 12/1981 | Hope, Sr. | |
| 4,746,828 A | 5/1988 | Nado et al. | |
| 4,782,832 A | 11/1988 | Trimble et al. | |
| 4,944,310 A | 7/1990 | Sullivan | |
| 5,028,216 A | 7/1991 | Harmsen et al. | |
| 6,149,382 A * | 11/2000 | Englander | F04D 29/059 |
| | | | 417/423.4 |
| 6,517,251 B1 | 2/2003 | Williams | |
| 6,532,959 B1 | 3/2003 | Berthon-Jones | |
| 6,581,594 B1 | 6/2003 | Drew et al. | |
| 6,802,648 B2 | 10/2004 | Merot et al. | |
| 6,864,609 B2 | 3/2005 | Fisher et al. | |
| 6,919,659 B2 | 7/2005 | Rapp | |
| 6,946,765 B2 | 9/2005 | Rapp et al. | |
| 6,998,746 B2 | 2/2006 | Simpson et al. | |
| 7,005,769 B1 | 2/2006 | Fisher et al. | |
| 7,605,508 B2 | 10/2009 | Baumgartner et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,807,840 B2 | 8/2014 | House et al. | |
| 8,888,447 B2 | 11/2014 | House et al. | |
| 9,845,860 B2 * | 12/2017 | Lannutti | F16H 55/48 |
| 10,137,264 B2 | 11/2018 | Darby et al. | |
| 10,148,152 B2 | 12/2018 | King et al. | |
| 10,286,167 B2 | 5/2019 | Bothma et al. | |
| 2007/0247009 A1 | 10/2007 | Hoffman et al. | |
| 2008/0304986 A1 | 12/2008 | Kenyon et al. | |
| 2009/0044808 A1 | 2/2009 | Guney et al. | |
| 2009/0050156 A1 | 2/2009 | Ng et al. | |
| 2009/0208354 A1 | 8/2009 | Crisi et al. | |
| 2009/0214145 A1 | 8/2009 | Cislo et al. | |
| 2010/0000534 A1 | 1/2010 | Kooij et al. | |
| 2012/0087816 A1 | 4/2012 | Zhang et al. | |
| 2012/0180792 A1 | 7/2012 | Cheng et al. | |
| 2012/0199129 A1 * | 8/2012 | Kenyon | A61M 16/0605 |
| | | | 128/205.25 |

| | | | |
|---|---|---|---|
| 2014/0154072 A1 | 6/2014 | Quartarone et al. | |
| 2014/0223725 A1 | 8/2014 | Hoffman | |
| 2015/0328418 A1 | 11/2015 | Bothma et al. | |
| 2017/0114833 A1 | 4/2017 | Herbst et al. | |
| 2017/0373545 A1 | 12/2017 | Zhong et al. | |
| 2018/0258944 A1 | 9/2018 | Diekmann et al. | |
| 2019/0036385 A1 | 1/2019 | Oikawa et al. | |
| 2019/0160239 A1 | 5/2019 | Darby et al. | |
| 2019/0334418 A1 | 10/2019 | Kenyon et al. | |
| 2020/0101245 A1 | 4/2020 | Bothma et al. | |
| 2024/0157071 A1 * | 5/2024 | Moir | A61M 16/021 |

FOREIGN PATENT DOCUMENTS

| | | |
|---|---|---|
| CN | 103906929 A | 7/2014 |
| CN | 209743188 U | 12/2019 |
| DE | 2 232 752 A1 | 1/1974 |
| DE | 103 47 361 A1 | 5/2005 |
| EP | 1 174 623 A2 | 1/2002 |
| EP | 3 409 173 A1 | 12/2018 |
| EP | 3 511 575 A1 | 7/2019 |
| GB | 1 418 716 | 12/1975 |
| JP | 60-85629 U | 6/1985 |
| JP | 6-53820 U | 7/1994 |
| JP | 2000-120670 A | 4/2000 |
| JP | 2003-148462 A | 5/2003 |
| JP | 2005-121230 A | 5/2005 |
| JP | 2009-107392 A | 5/2009 |
| JP | 2016-223428 A | 12/2016 |
| JP | 2018-519925 A | 7/2018 |
| JP | 2019-514558 A | 6/2019 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2007/134405 A1 | 11/2007 |
| WO | WO 2008/051534 A2 | 5/2008 |
| WO | WO 2009/052560 A1 | 4/2009 |
| WO | WO 2010/135785 A1 | 12/2010 |
| WO | WO 2011/062633 A1 | 5/2011 |
| WO | WO 2012/113027 A1 | 8/2012 |
| WO | WO 2012/145358 A2 | 10/2012 |
| WO | WO 2012/171072 A1 | 12/2012 |
| WO | WO 2013/020167 A1 | 2/2013 |
| WO | WO 2017/006189 A1 | 1/2017 |
| WO | WO 2020/208603 A1 | 10/2020 |

OTHER PUBLICATIONS

Notice of Reasons for Refusal mailed Apr. 1, 2024 in Japanese Application No. 2022-552956, with English translation, 11 pages.
"*Respiratory Physiology*", by John B. West, Lippincott Williams & Wilkins, 9th edition published 2012 (8 pages).
Written Opinion of the International Searching Authority mailed Jun. 1, 2021 in International Application No. PCT/US2021/020656, 9 pages.
International Search Report Mailed Jun. 1, 2021 in International Application No. PCT/US2021/020656, 12 pages.
Notice of Reasons for Refusal mailed Oct. 10, 2023 in Japanese Application No. 2022-552956, with English translation, 15 pages.
First Office Action mailed Apr. 15, 2025 in Chinese Application No. 202180027944.6, with English translation, 13 pages.

* cited by examiner

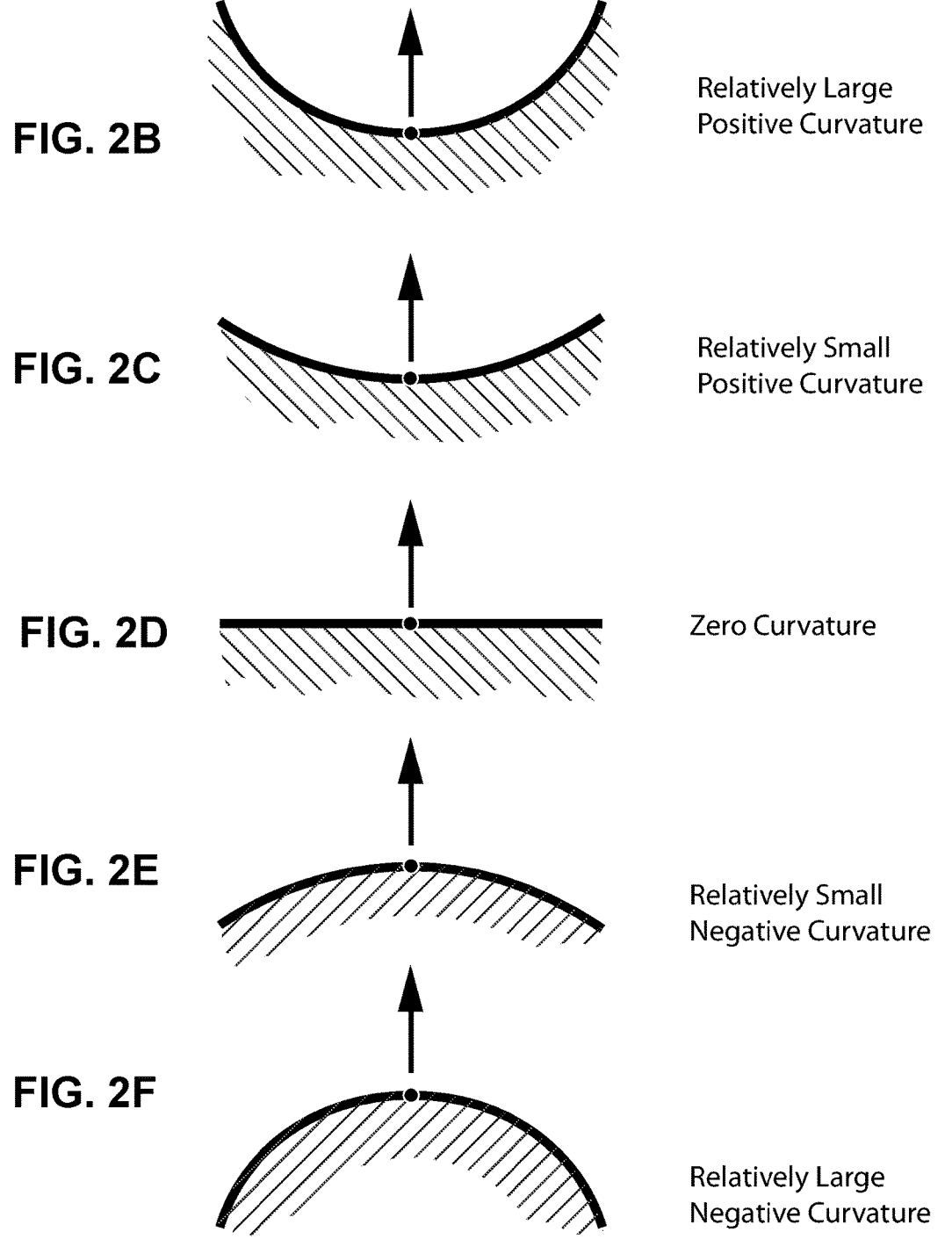
FIG. 2B          Relatively Large
                     Positive Curvature
FIG. 2C          Relatively Small
                     Positive Curvature
FIG. 2D          Zero Curvature
FIG. 2E          Relatively Small
                     Negative Curvature
FIG. 2F          Relatively Large
                     Negative Curvature

6000

6088

BEARING SLEEVE FOR BLOWER

1 CROSS-REFERENCE TO RELATED APPLICATIONS

This application is the U.S. national phase of International Application No. PCT/US2021/020656 filed Mar. 3, 2021 which designated the U.S. and claims priority to U.S. Provisional Patent Application No. 62/984,515 filed Mar. 3, 2020, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use. The present technology also relates to a blower for generating a pressure differential and/or to a pressure generating device or respiratory pressure therapy (RPT) device, e.g., used for the delivery of respiratory therapy to a patient.

2.2 Description of the Related Art

2.2.1 Human Respiratory System and Its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure.

Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH₂O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed StellarT™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical. Recently, companies that manufacture large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses or "boli", each bolus timed to coincide with the onset of inhalation. This therapy mode is known as pulsed oxygen delivery (POD) or demand mode, in contrast with traditional continuous flow delivery more suited to stationary oxygen concentrators.

2.2.3.6 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology relates to a blower for generating a pressurized flow of gas.

Another aspect of the present technology relates to a motor-blower comprising a motor and a centrifugal fan, the centrifugal fan comprising an impeller and a housing, the housing comprising a housing inlet and a housing outlet, the motor-blower configured to receive the flow of air at the housing inlet at a pressure lower than ambient pressure and to direct it to the housing outlet at a pressure higher than ambient pressure in use, the motor having a shaft constructed and arranged to rotate in use about a shaft axis, the impeller constructed and arranged to rotate in use about the shaft axis, the impeller comprising a plurality of blades, the housing inlet having a housing inlet centre lying on the shaft axis and the housing outlet having a housing outlet centre lying on the shaft axis.

Another aspect of the present technology relates to an apparatus for providing positive pressure respiratory therapy to a patient breathing in a respiratory cycle including an inhalation portion and an exhalation portion. The apparatus includes: a controllable motor-blower configured to generate a supply of air at a positive pressure relative to ambient pressure by rotating one or more impellers at an impeller speed; a housing holding the motor-blower, the housing comprising an inlet and a patient-connection port, the patient-connection port being structured to communicate the supply air at the positive pressure from the motor-blower to a patient interface via an air circuit in use; a sensor to monitor at least one of pressure and a flow rate of the supply of air at positive pressure and to generate a sensor output; and a controller configured to adjust an operating parameter of the motor-blower in accordance with the sensor output to maintain a minimum positive pressure in the patient interface during a treatment session by causing an increase in the impeller speed during the inhalation portion of the respiratory cycle and causing a decrease in the impeller speed during the exhalation portion of the breathing cycle.

An aspect of the present technology relates to a motor including a shaft constructed and arranged to rotate in use about a shaft axis and at least one bearing to rotatably support the shaft.

An aspect of the present technology relates to an RPT device including a blower, e.g., used for the delivery of respiratory therapy to a patient.

An aspect of the present technology relates to a blower including an elastomeric bearing sleeve structured and arranged to support and retain a bearing.

An aspect of the present technology relates to an elastomeric bearing sleeve structured and arranged to support and retain a bearing.

An aspect of the present technology relates to a blower including a stationary component and an elastomeric bearing sleeve comprising an overmolded connection to the stationary component.

An aspect of the present technology relates to a blower including a rotor, a motor adapted to drive the rotor, at least one bearing to rotatably support the rotor, a stationary component, and a bearing sleeve provided to the stationary component. The bearing sleeve is structured and arranged to support and retain the bearing to the stationary component. The bearing sleeve comprises an elastomeric material, and the bearing sleeve comprises one or more bumps or ribs configured to engage along an outer race of the bearing.

An aspect of the present technology relates to a blower including a rotor, a motor adapted to drive the rotor, at least one bearing to rotatably support the rotor, a stationary component, and a bearing sleeve provided to the stationary component. The bearing sleeve is structured and arranged to support and retain the bearing to the stationary component. The bearing sleeve comprises an elastomeric material, and the bearing sleeve comprises an overmolded connection to the stationary component. The bearing sleeve comprises a retaining structure structured and arranged to form a mechanical connection to the stationary component.

An aspect of the present technology relates to a blower including a rotor, a motor adapted to drive the rotor, at least one bearing to rotatably support the rotor, a biasing element to provide a pre-load force to the at least one bearing, a stationary component, and a bearing sleeve provided to the stationary component. The bearing sleeve is structured and arranged to support and retain the bearing to the stationary component. The bearing sleeve comprises an elastomeric material. The bearing sleeve is structured to protrude past the bearing and provide a space for enclosing and positioning the biasing element.

An aspect of one form of the present technology is a method of manufacturing apparatus.

An aspect of one form of the present technology is a portable RPT device that may be carried by a person, e.g., around the home of the person.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Patient Interface

FIG. 2A shows a patient interface in the form of a nasal mask in accordance with one form of the present technology.

FIG. 2B shows a schematic of a cross-section through a structure at a point. An outward normal at the point is indicated. The curvature at the point has a positive sign, and a relatively large magnitude when compared to the magnitude of the curvature shown in FIG. 2C.

FIG. 2C shows a schematic of a cross-section through a structure at a point. An outward normal at the point is indicated. The curvature at the point has a positive sign, and a relatively small magnitude when compared to the magnitude of the curvature shown in FIG. 2B.

FIG. 2D shows a schematic of a cross-section through a structure at a point. An outward normal at the point is indicated. The curvature at the point has a value of zero.

FIG. 2E shows a schematic of a cross-section through a structure at a point. An outward normal at the point is indicated. The curvature at the point has a negative sign, and a relatively small magnitude when compared to the magnitude of the curvature shown in FIG. 2F.

FIG. 2F shows a schematic of a cross-section through a structure at a point. An outward normal at the point is indicated. The curvature at the point has a negative sign, and a relatively large magnitude when compared to the magnitude of the curvature shown in FIG. 2E.

4.3 RPT Device

Figure 3A:
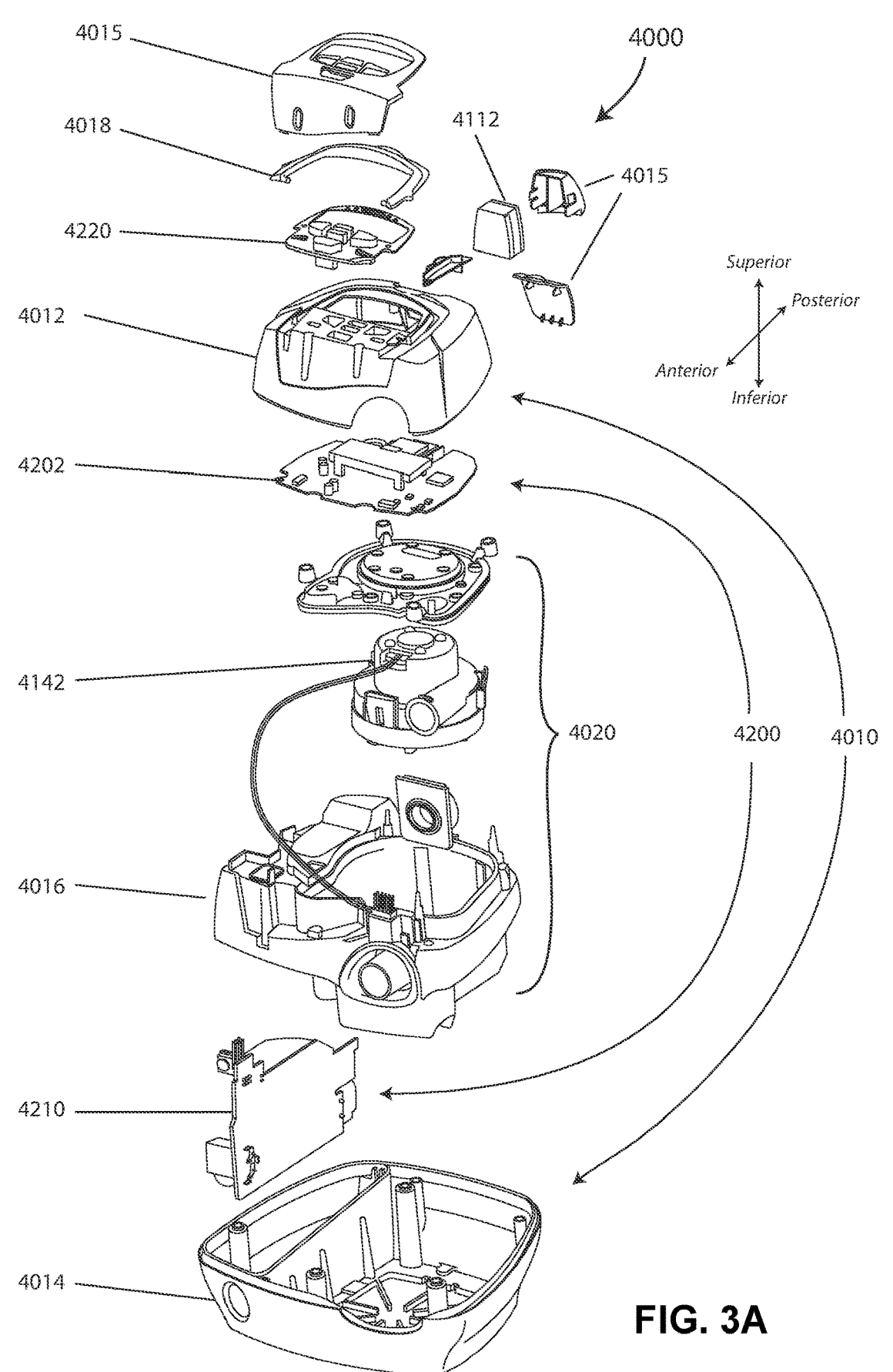

FIG. 3A shows an RPT device in accordance with one form of the present technology.

Figure 3B:
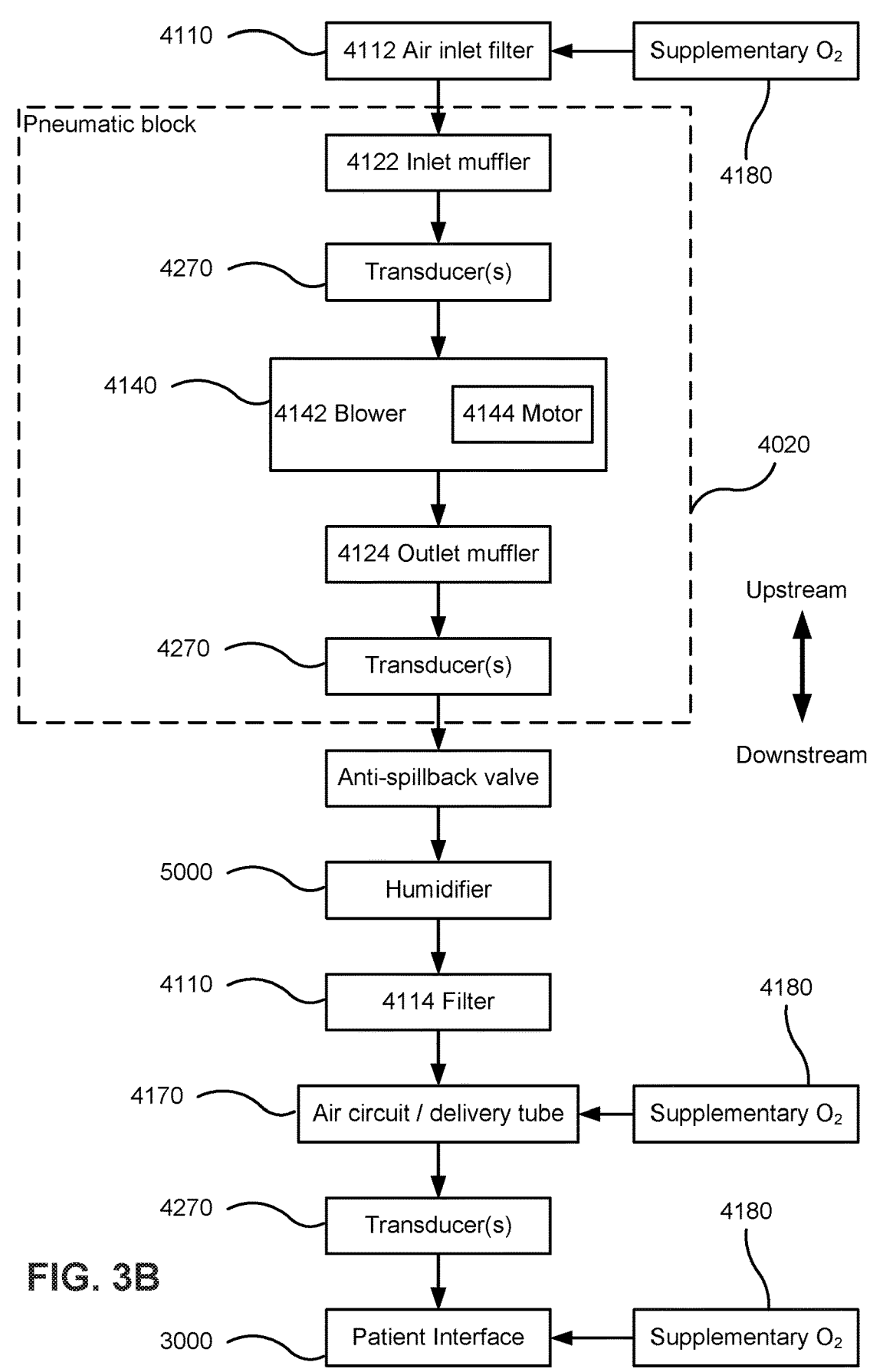

FIG. 3B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 3C:
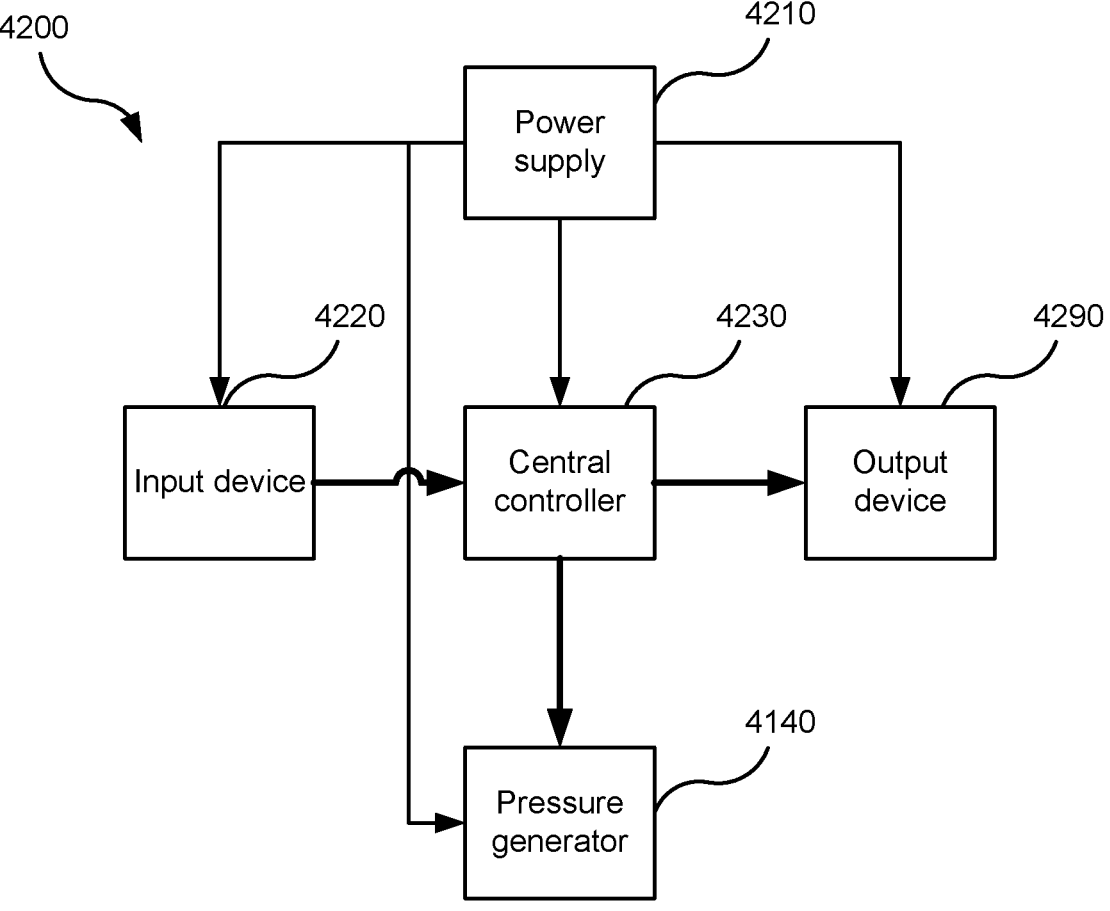

FIG. 3C is a schematic diagram of the electrical components of an RPT device in accordance with one form of the present technology.

Figure 4:
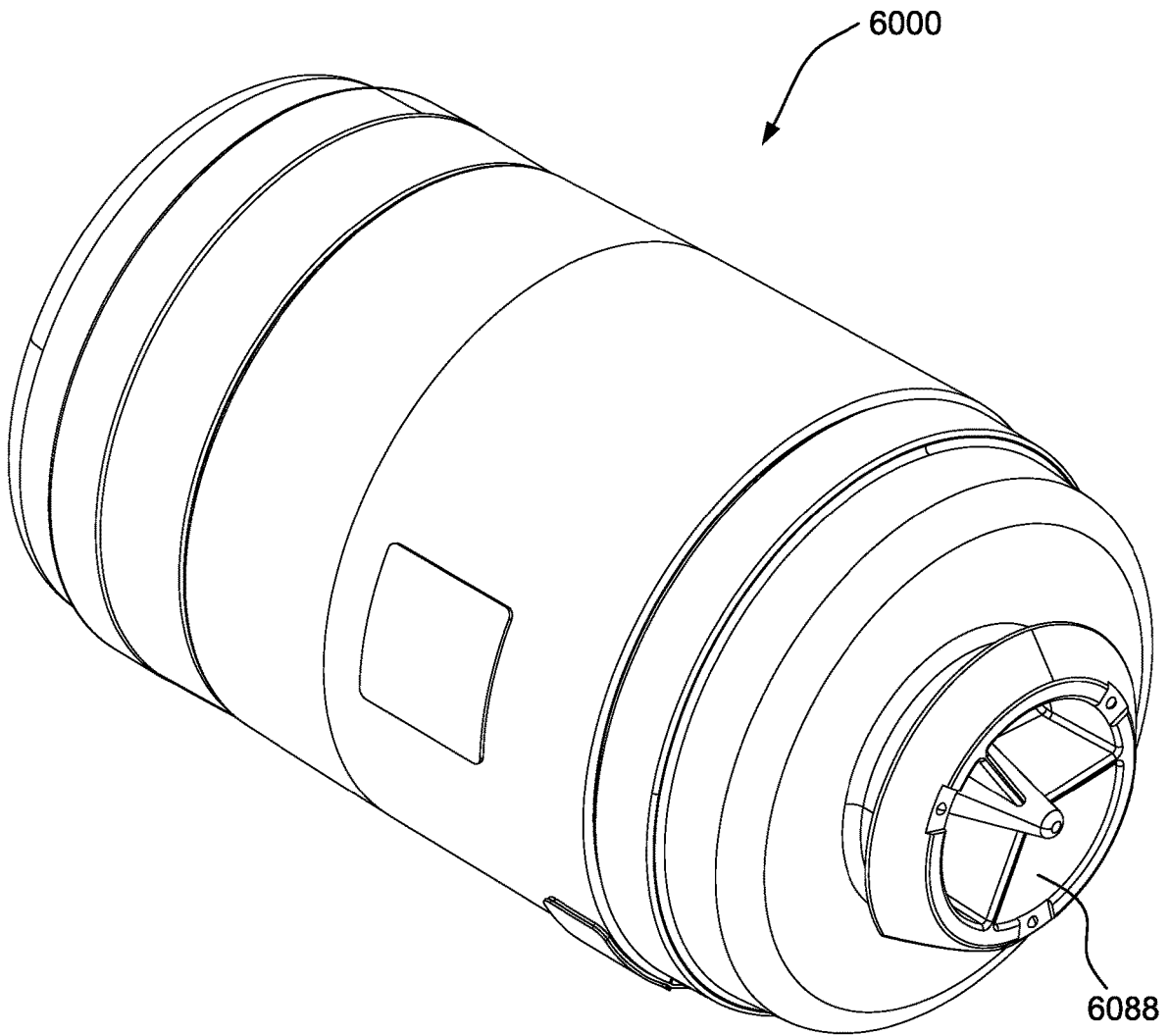

FIG. 4 is a perspective view of a blower for an RPT device according to an example of the present technology.

Figure 5:
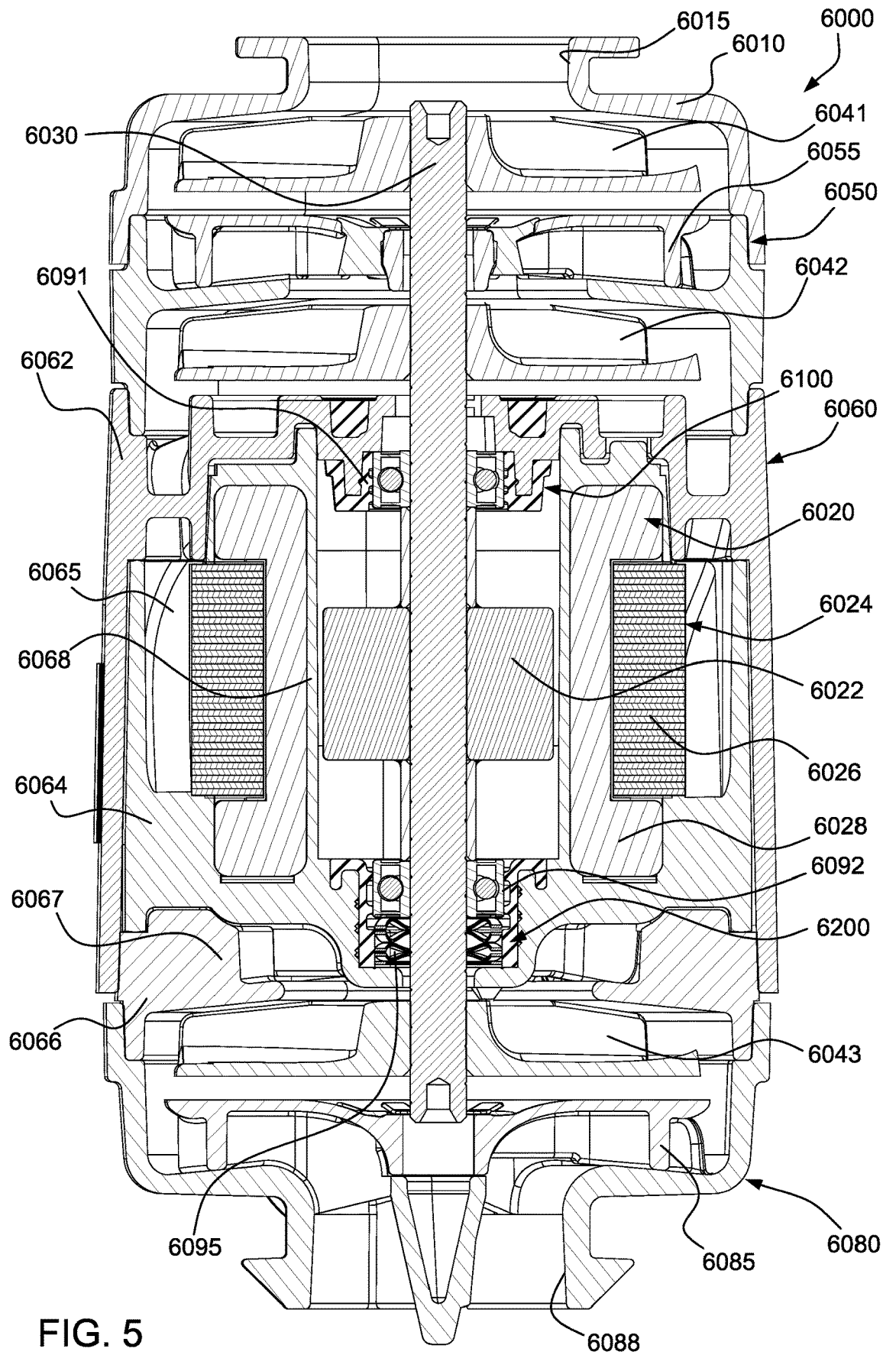

FIG. 5 is a cross-sectional view of the blower of FIG. 4.

Figure 6:
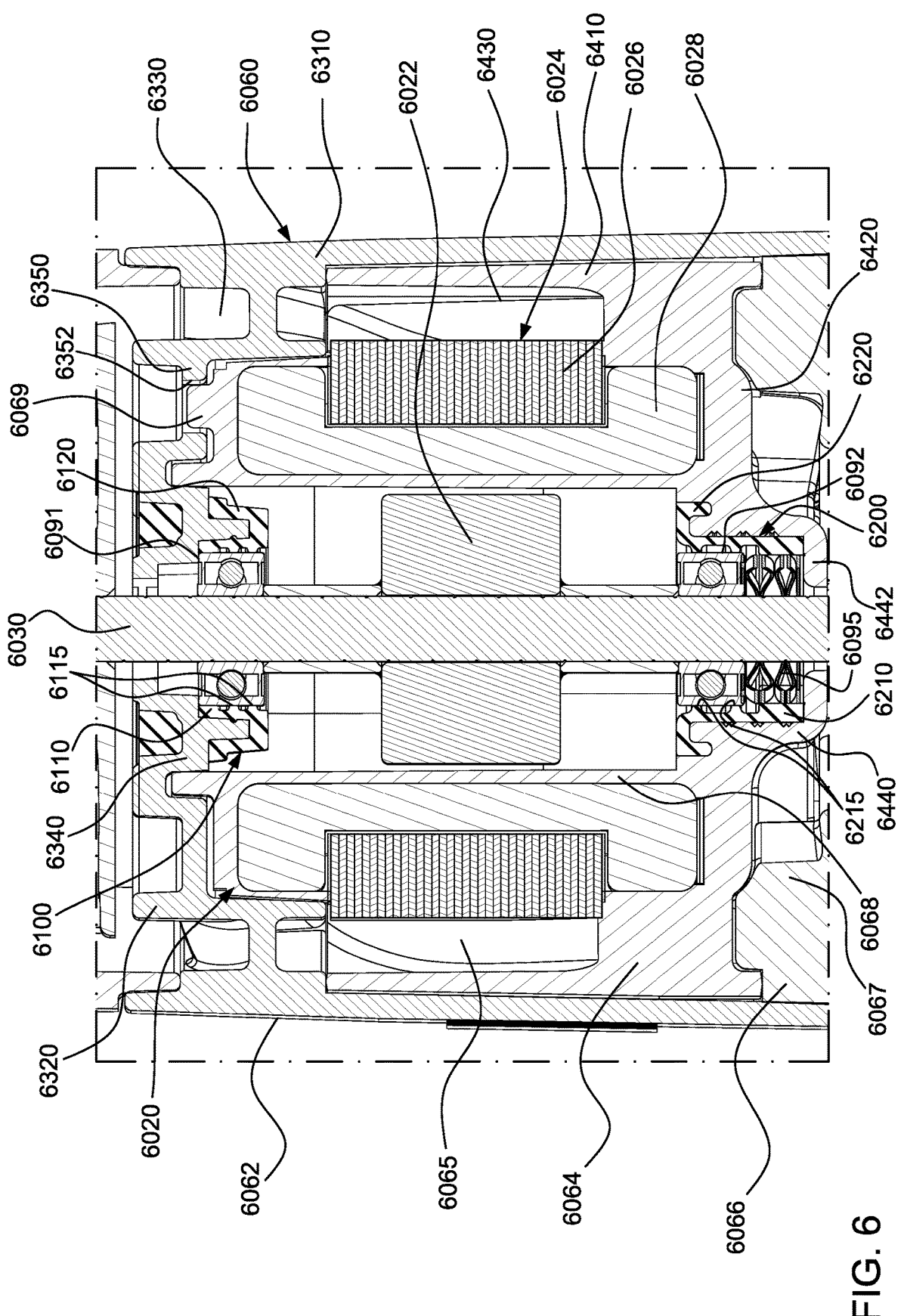

FIG. 6 is an enlarged view of a portion of the blower shown in FIG. 5.

Figure 7:
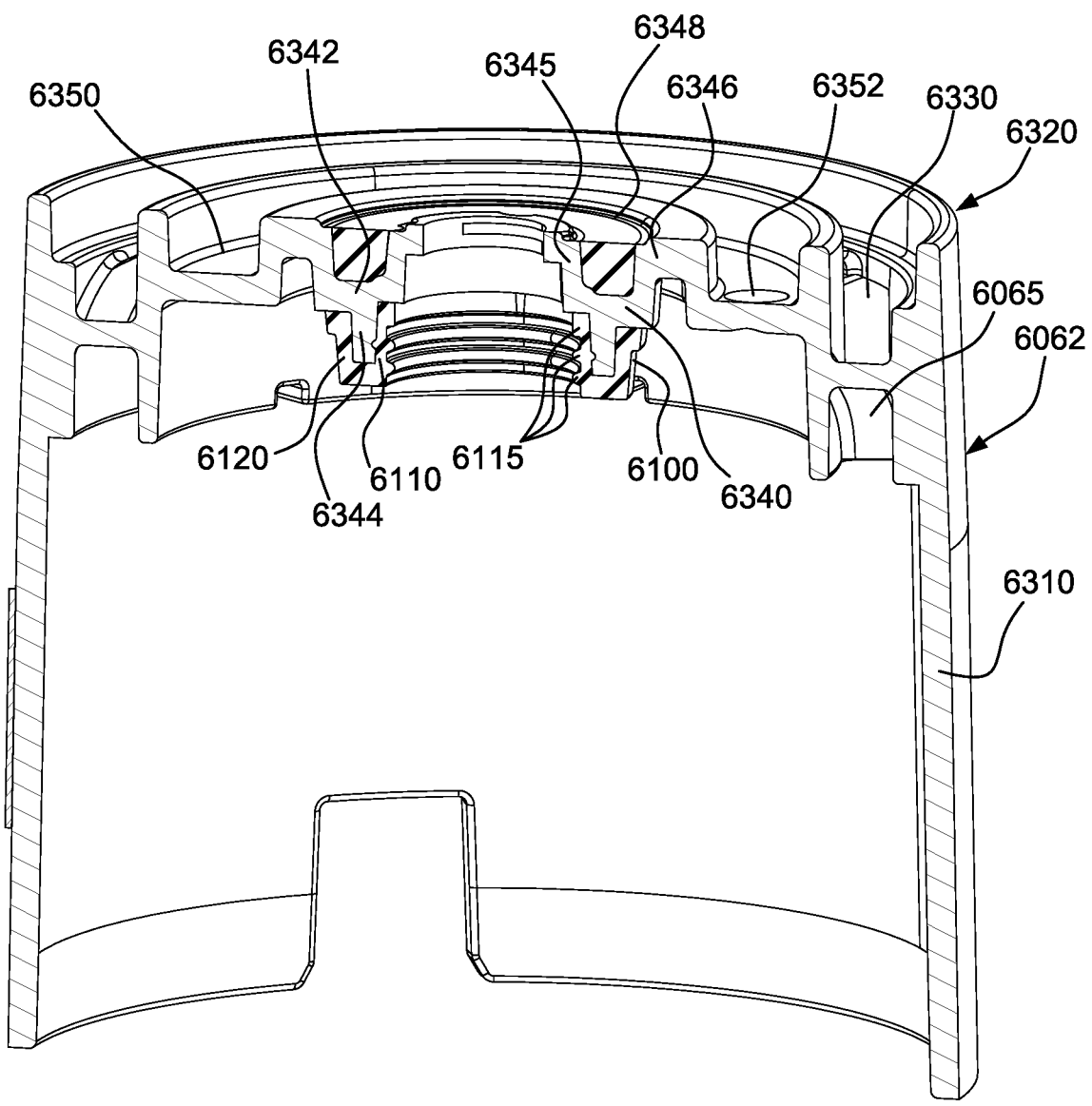

FIG. 7 is a cross-sectional view showing an upper end portion and bearing sleeve of a stationary component for a blower according to an example of the present technology.

Figure 8:
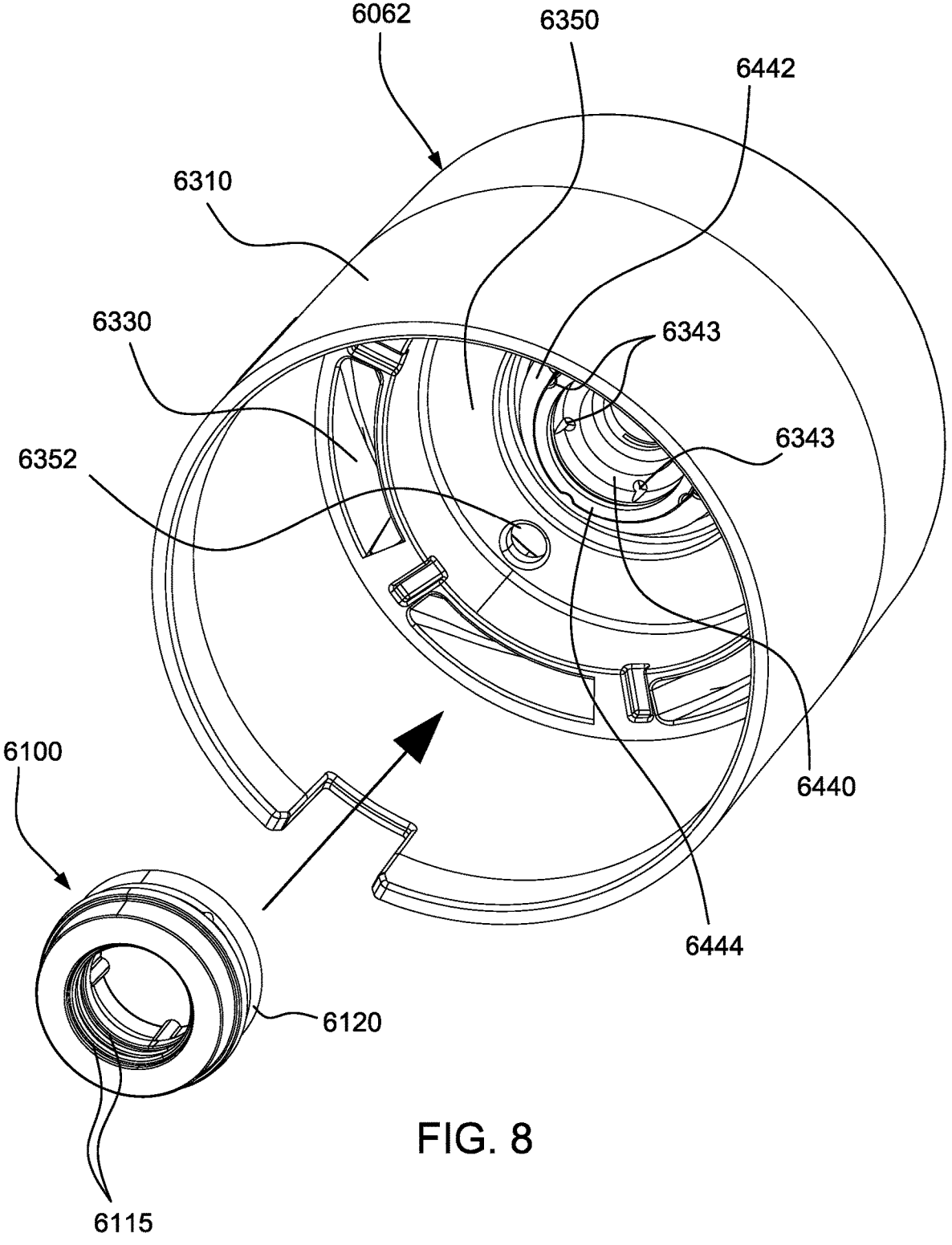

FIG. 8 is an exploded view showing an upper end portion and bearing sleeve of a stationary component for a blower according to an example of the present technology.

Figure 9:
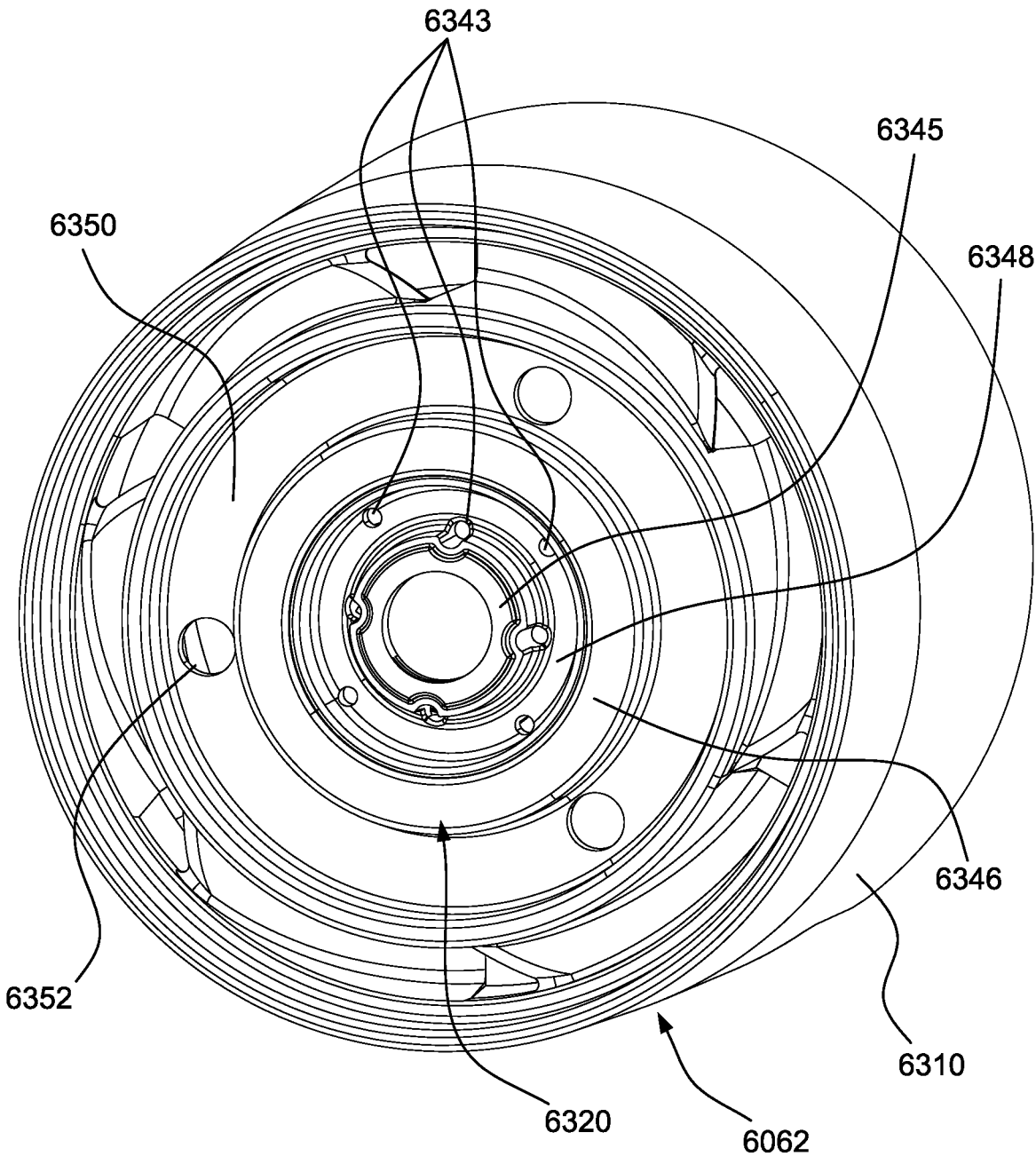

FIG. 9 is a top perspective view of an upper end portion of a stationary component for a blower according to an example of the present technology.

Figure 10:
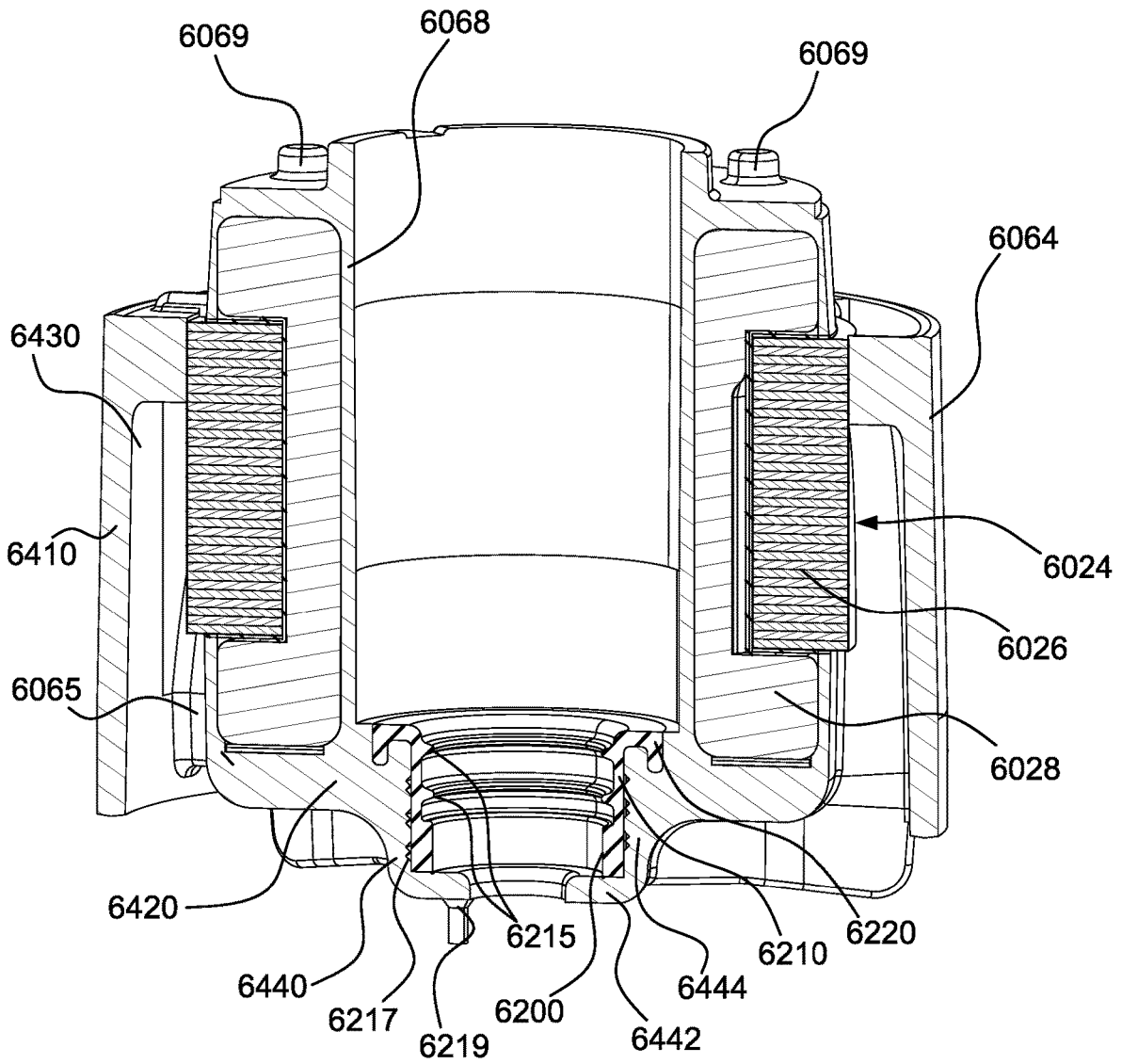

FIG. 10 is cross-sectional view showing an intermediate portion and bearing sleeve of a stationary component for a blower according to an example of the present technology.

Figure 11:
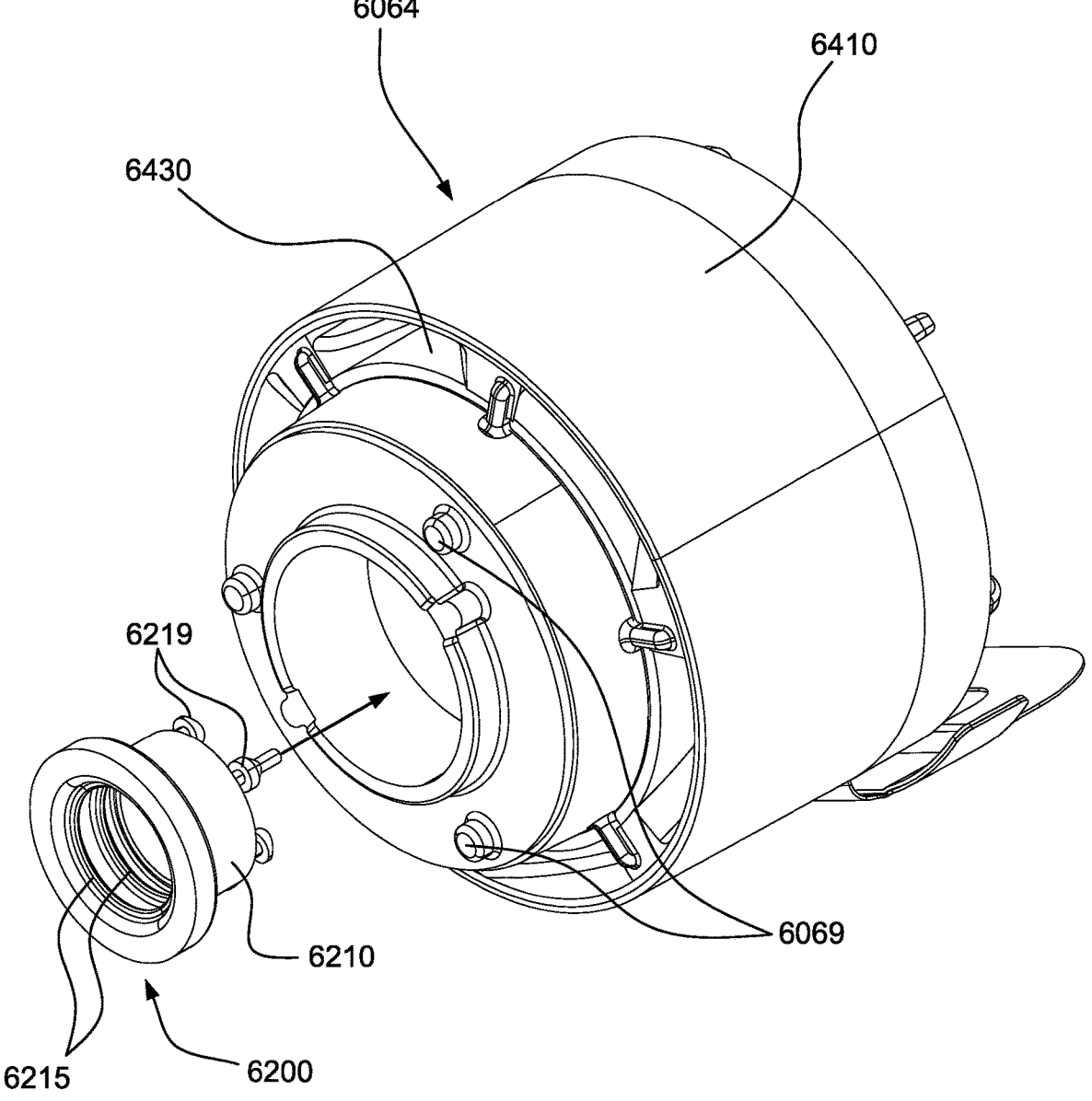

FIG. 11 is an exploded view showing an intermediate portion and bearing sleeve of a stationary component for a blower according to an example of the present technology.

Figure 12:
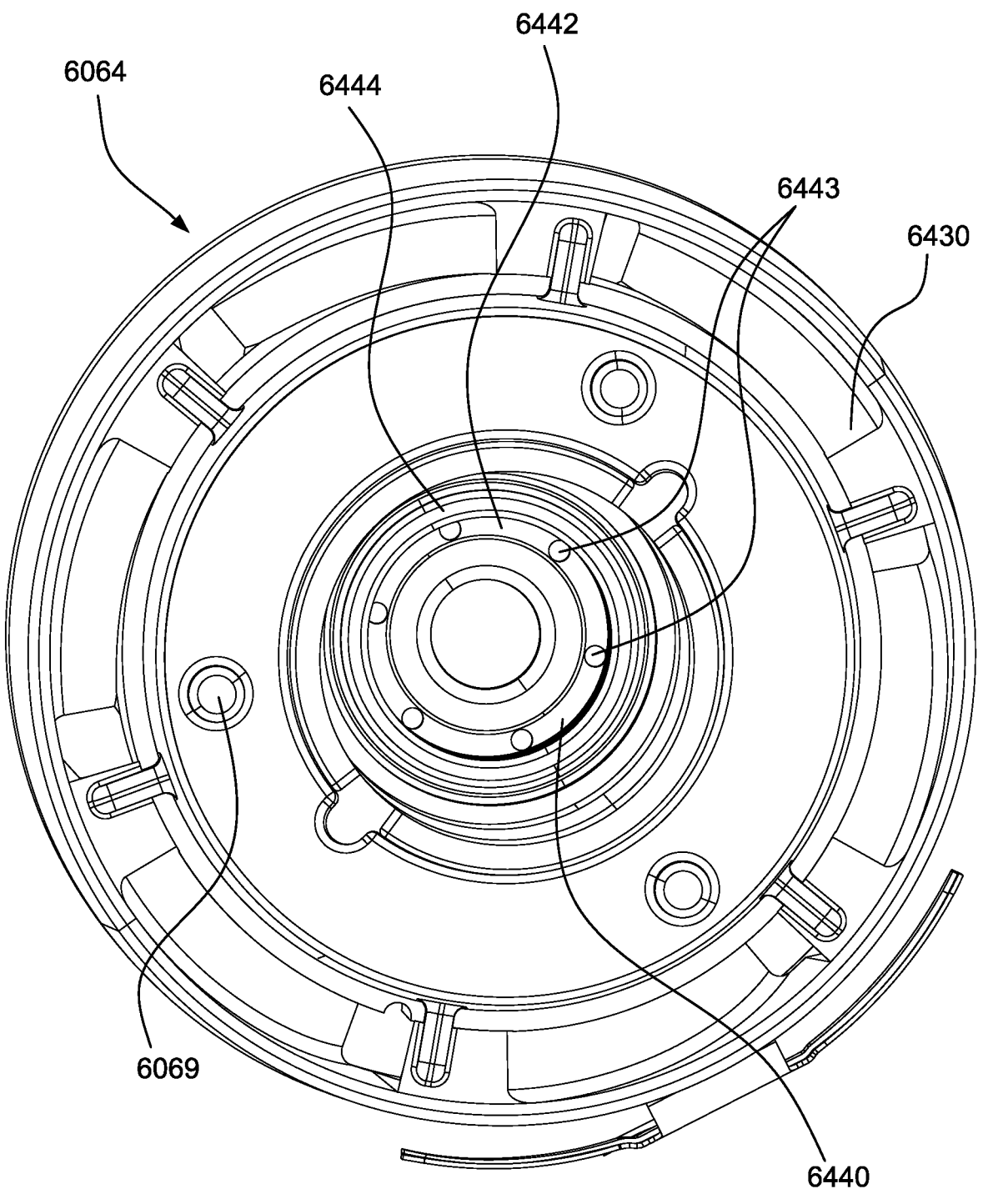

FIG. 12 is a top perspective view of an intermediate portion of a stationary component for a blower according to an example of the present technology.

Figure 13:
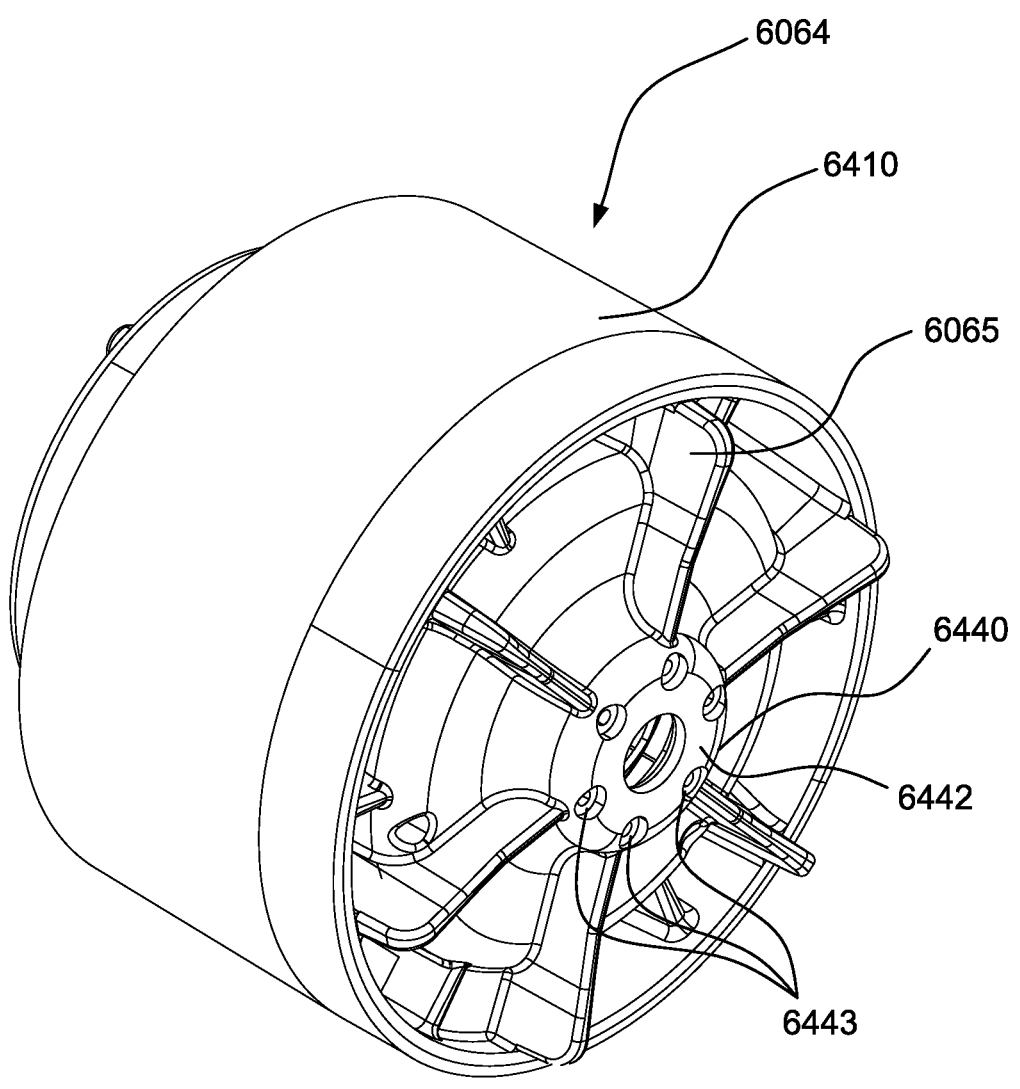

FIG. 13 is a bottom perspective view of an intermediate portion of a stationary component for a blower according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000, e.g., see FIG. 1.

5.3 Patient Interface

Figure 2A:
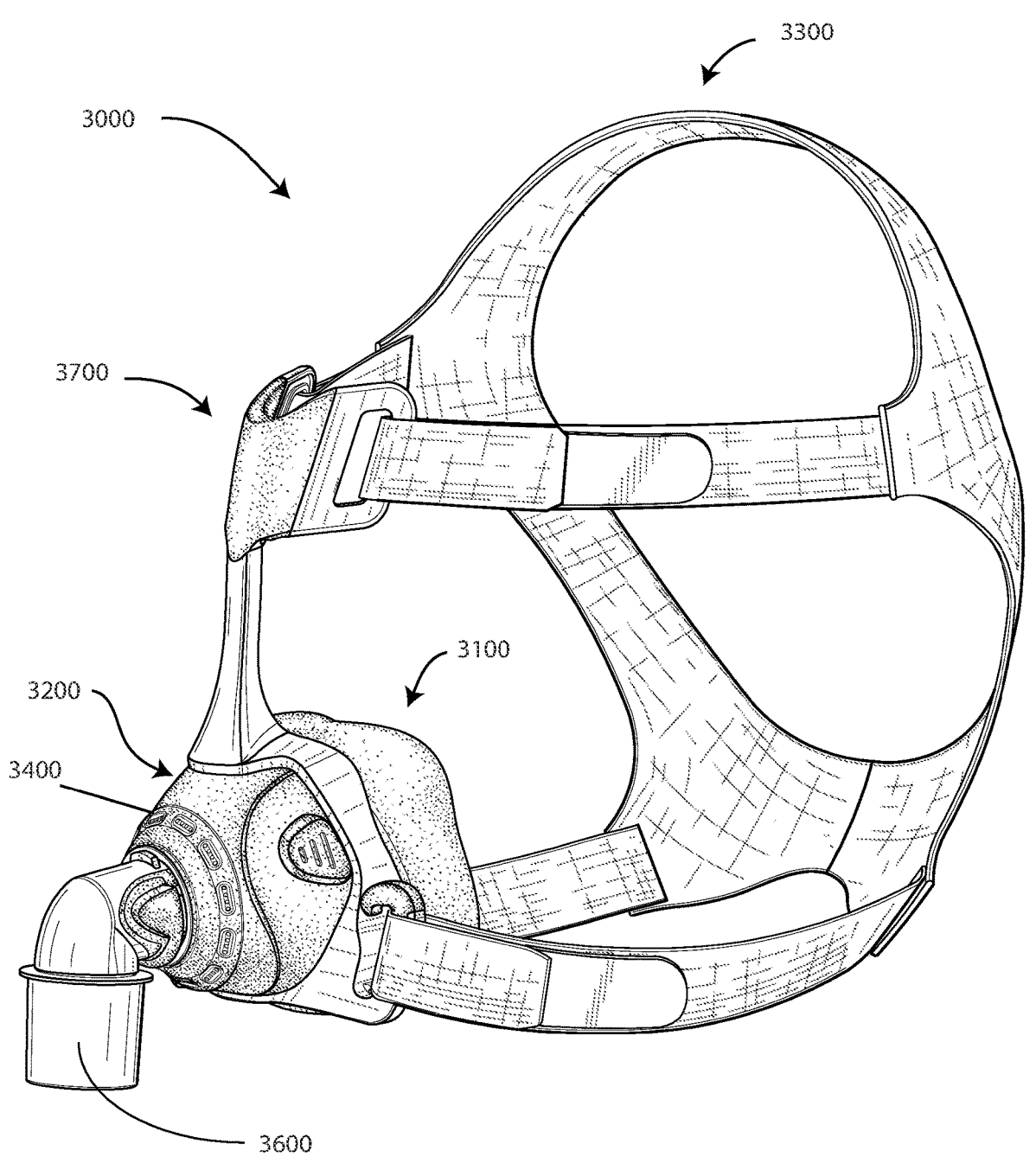
FIG. 2G shows the surface of a structure, with a one dimensional hole in the surface. The illustrated plane curve forms the boundary of a one dimensional hole.
FIG. 2H shows a cross-section through the structure of FIG. 2G. The illustrated surface bounds a two dimensional hole in the structure of FIG. 2G.
FIG. 2I shows a perspective view of the structure of FIG. 2G, including the two dimensional hole and the one dimensional hole. Also shown is the surface that bounds a two dimensional hole in the structure of FIG. 2G.

FIG. 2A shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.4 RPT Device

FIGS. 3A to 3C show an RPT device 4000 in accordance with one aspect of the present technology comprising mechanical, pneumatic, and/or electrical components and configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., one or more filters 4110 (e.g., an inlet air filter 4112, an air outlet filter 4114), an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller, a pressure generator 4140, one or more protection circuits, memory, transducers 4270, data communication interface and one or more output devices 4290. Electrical components 4200 may be mounted on a single Printed Circuit Board Assembly (PCBA) 4202. In an alternative form, the RPT device 4000 may include more than one PCBA 4202.

Pressure Generator

In one form of the present technology, the pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866, 944; 8,638,014; 8,636,479; and PCT Patent Application Publication No. WO 2013/020167.

The pressure generator 4140 may be under the control of the central controller 4230 and/or a therapy device controller.

In other forms, a pressure generator 4140 may be a piston-driven pump, a pressure regulator connected to a high pressure source (e.g. compressed air reservoir), or a bellows.

FIGS. 4 to 13 show a blower 6000 for producing a flow, or a supply, of air at positive pressure according to an example of the present technology. In the illustrated example, the blower 6000 provides an axially symmetric, three-stage blower design. In an example, the blower 6000 may be structured to provide pressurized air up to 45-50 cmH$_2$O, e.g., in the range of 2-50 cmH$_2$O, e.g., 3-45 cmH$_2$O, 4-30 cmH$_2$O.

As best shown in FIGS. 5 and 6, the blower 6000 includes an inlet cover 6010 providing an axial air inlet 6015 (blower inlet), a motor 6020 adapted to drive a rotatable shaft or rotor 6030, first and second impellers 6041, 6042 provided to the rotor 6030 and positioned on one side of the motor 6020 and a third impeller 6043 provided to the rotor 6030 and positioned on the opposite side of the motor 6020. The blower 6000 includes a first stationary component 6050 including stage 1 stator vanes 6055 and following the first impeller 6041, a second stationary component 6060 including stage 2 stator vanes 6065, 6067 following the second impeller 6042 and enclosing the motor 6020, and a third stationary component 6080 including stage 3 stator vanes 6085 and following the third impeller 6043. The third stationary component 6080 also provides an axial air outlet 6088 (blower outlet). In use, the blower 6000 is operable to draw a supply of air into the blower inlet 6015 and provide a pressurized supply of air at the blower outlet 6088.

The motor 6020 includes a magnet 6022 provided to the rotor 6030 and a stator assembly 6024. The stator assembly 6024 includes a lamination stack 6026 (e.g., a plurality of laminations (e.g., constructed of iron)) and a stator coil or windings 6028 (e.g., constructed of copper) provided to the lamination stack 6026.

The second stationary component 6060 includes a tube portion 6068 that encloses the magnet 6022 on the rotor 6030 which is aligned in close proximity to the stator assembly 6024 provided along an exterior surface of the tube portion 6068. The tube portion 6068 is constructed of a material that is sufficiently "magnetically transparent" to allow a magnetic field to pass through it, which allows the stator assembly 6024 along its exterior surface to act on the magnet 6022 positioned within the tube portion 6068. Further details and examples of such arrangement are disclosed in U.S. Patent Publication No. US-2008-0304986, which is incorporated herein by reference in its entirety.

Further examples and details of such blower arrangement are described in PCT Publication No. WO 2013/020167, which is incorporated herein by reference in its entirety.

In the illustrated example, the rotor 6030 is rotatably supported by a pair of bearings 6091, 6092, e.g., ball bearings, that are retained or supported by the second stationary component 6060.

In the illustrated example, e.g., see FIG. 5, the second stationary component 6060 is provided in three parts that are formed separately from one another (e.g., molded) and then assembled to one another (e.g., heat stake, mechanical interlock (e.g., tongue/groove), friction-fit, etc.). As illustrated, the second stationary component 6060 includes an upper end portion 6062 (also referred to as an end bell), an intermediate portion 6064, and a lower end portion 6066. As described below, an upper bearing sleeve 6100 (e.g., comprising an elastomeric material, e.g., thermo-plastic elastomer (TPE), thermo-plastic polyurethane (TPU)) is provided to the upper end portion 6062 that is structured and arranged to support and retain an upper one of the pair of bearings (i.e., the bearing 6091 on a side of the second stationary component 6060 that is closer to the blower inlet 6015), and a lower bearing sleeve 6200 (e.g., comprising an elastomeric material, e.g., TPE, TPU) is provided to the intermediate portion 6064 that is structured and arranged to support and retain a lower one of the pair of bearings (i.e., the bearing 6092 on a side of the second stationary component 6060 that is closer to the blower outlet 6088).

As best shown in FIG. 6, the upper end portion 6062 and the intermediate portion 6064 cooperate to support and maintain the motor 6020 in an operative position. In addition, the upper end portion 6062 and the intermediate portion 6064 cooperate to form stage 2 stator vanes 6065 structured to direct airflow in a generally axial direction down and around the motor 6020, i.e., the upper end portion 6062 includes a first set of vanes that form an upper portion of each stator vane 6065 and the intermediate portion 6064 includes a second set of vanes that form a lower portion of each stator vane 6065. The lower end portion 6066 is positioned below the motor 6020 and includes stage 2 stator vanes 6067 structured to direct air flow in a radial direction to the third stage, e.g., see FIG. 5. Further examples and details of such stator arrangement are described in PCT Publication No. WO 2013/020167, which is incorporated herein by reference in its entirety.

As shown in FIGS. 6 to 9, the upper end portion 6062 includes a cylindrical side wall 6310 which encloses the intermediate portion 6064 and forms an outer wall of the blower 6000, and an end wall 6320 provided to an upper end of the cylindrical side wall 6310. The end wall 6320 provides a radially outer, opening 6330 that supports the first set of vanes that form an upper portion of each stator vane 6065, and a radially inner, support portion 6340 that supports and retains the upper bearing sleeve 6100.

The end wall 6320 also includes an intermediate connection portion 6350 (between the radially outer, opening 6330 and the radially inner, support portion 6340) that connects to the intermediate portion 6064. For example, the intermediate connection portion 6350 may be connected to the intermediate portion 6064 via heat staking, e.g., the intermediate portion 6064 includes stakes 6069 configured and arranged to extend through respective openings 6352 in the intermediate connection portion 6350 and subsequently heat staked to secure the upper end portion 6062 to the intermediate portion 6064. However, it should be appreciated that the upper end portion 6062 and the intermediate portion 6064 may be connected to one another in other suitable manners.

In the illustrated example, the support portion 6340 includes a base wall 6342 and a support wall 6344 extending axially inwardly from an inner side of the base wall 6342. In addition, the base wall 6342, along with spaced-apart side walls 6345, 6346 extending axially outwardly from an outer side of the base wall 6342, forms a channel 6348.

As illustrated, the upper bearing sleeve 6100 is supported and retained by the support portion 6340. The upper bearing sleeve 6100 includes a cylindrical or tubular side wall 6110 providing a cylindrical opening to support and retain the upper one of the pair of bearings, i.e., the bearing 6091. Also, as illustrated, the cylindrical or tubular side wall 6110 is arranged along a radially inner side of the support wall 6344. Further, the upper bearing sleeve 6100 includes a retaining structure 6120 that wraps around the support wall 6344 and into the channel 6348 to retain the upper bearing sleeve 6100 to the support portion 6340 of the upper end portion 6062.

In the illustrated example, the cylindrical or tubular side wall 6110 includes one or more annular bumps or ribs 6115 (e.g., 2, 3, 4, or more bumps or ribs) for retaining the bearing 6091 in an operative position. As illustrated, the bumps or ribs 6115 are configured and arranged to engage along an outer race of the bearing 6091. The inner race of the bearing 6091 is configured and arranged to engage the rotor 6030.

In the illustrated example, the cylindrical side wall 6110 includes one or more annular bumps or ribs 6115 (e.g., 2, 3, 4, or more bumps or ribs) for retaining the bearing 6091 in an operative position. As illustrated, the bumps or ribs 6115 are configured and arranged to engage along an outer race of the bearing 6091. The inner race of the bearing 6091 is configured and arranged to engage the rotor 6030.

In an example, the upper bearing sleeve 6100 is constructed of an elastomeric material, e.g., TPE, TPU. The upper bearing sleeve 6100 is arranged between the support portion 6340 and the bearing 6091, e.g., to isolate vibrations, reduce noise, and provide shock absorption, e.g., in the radial direction. Also, the upper bearing sleeve 6100 takes the place of damping or bearing grease, e.g., between the support portion 6340 and the bearing 6091, which facilitates manufacturing.

The upper bearing sleeve 6100 may be permanently (e.g., overmolded) or removably (e.g., interference fit assembly) connected to the support portion 6340 of the upper end portion 6062.

In the illustrated example, the upper bearing sleeve 6100 and the upper end portion 6062 comprise an overmolded construction to form a one-piece, integrated component. For example, the upper end portion 6062 may comprise a first part or base mold and the upper bearing sleeve 6100 may comprise a second part or overmold that is provided (e.g., by overmolding) to the first part. In an example, the upper end portion 6062 comprises a material (e.g., polycarbonate, polypropylene) that is more rigid than the upper bearing sleeve 6100, e.g., TPE, TPU.

In an example, the upper bearing sleeve 6100 may be overmolded to the upper end portion 6062 so that the retaining structure 6120 provides an interference fit or mechanical interlock with the upper end portion 6062. For example, the base wall 6342 of the support portion 6340 includes a plurality of holes 6343 so that, during the overmolding process, the elastomeric material of the upper bearing sleeve 6100 can flow into and fill the channel 6348, flow through the holes, and flow around the support wall 6344 to mechanically secure the upper bearing sleeve 6100 to the upper end portion 6062. Also, the outer side of the cylindrical or tubular side wall 6110 may include one or threads or protrusions adapted to engage within respective grooves provided to the support wall 6344 to further secure the upper bearing sleeve 6100 in an operative position. In addition, in an example, the elastomeric material of the upper bearing sleeve 6100 may provide interfacing surfaces that bond or stick to the upper end portion 6062 to enhance the connection with the upper end portion 6062.

As shown in FIGS. 10 to 13, the intermediate portion 6064 includes the tube portion 6068, a cylindrical side wall

6410 which provides a radially outer, opening 6430 that supports the second set of vanes that form a lower portion of each stator vane 6065, and an end wall 6420 provided to a lower end of the tube portion 6068. The end wall 6420 provides a support portion 6440 that supports and retains the lower bearing sleeve 6200. In the illustrated example, the intermediate portion 6064 may be overmolded to the stator assembly 6024, and may together be referred to as a stator overmold.

In the illustrated example, the support portion 6440 includes a base wall 6442 and a support wall 6444 extending axially inwardly from an inner side of the base wall 6442.

As illustrated, the lower bearing sleeve 6200 is supported and retained by the support portion 6440. The lower bearing sleeve 6200 includes a cylindrical or tubular side wall 6210 providing a cylindrical opening to support and retain the lower one of the pair of bearings, i.e., the bearing 6092. Also, as illustrated, the cylindrical or tubular side wall 6210 is arranged along a radially inner side of the support wall 6444. Further, the lower bearing sleeve 6200 includes a retaining structure 6220 that wraps around the support wall 6444 to retain the lower bearing sleeve 6200 to the support portion 6440 of the intermediate portion 6064.

In the illustrated example, the cylindrical or tubular side wall 6210 includes an elongated configuration, and an upper side of the cylindrical or tubular side wall 6210 includes one or more annular bumps or ribs 6215 (e.g., 2, 3, 4, or more bumps or ribs) for retaining the bearing 6092 in an operative position. As illustrated, the bumps or ribs 6215 are configured and arranged to engage along an outer race of the bearing 6092. The inner race of the bearing 6092 is configured and arranged to engage the rotor 6030.

In the illustrated example, the lower side of the cylindrical or tubular side wall 6210 (adjacent the base wall 6442) is devoid of any bumps or ribs, which lower side protrudes past the bearing 6092 and provides a space for enclosing and positioning a spring or biasing element 6095. As illustrated, the spring or biasing element 6095 is arranged between the base wall 6442 and the bearing 6092 to apply a pre-load force to the bearing 6092 (e.g., pre-load to an inner race of the ball bearing 6092) and/or maintain alignment of the magnet 6022 with the stator assembly 6024.

In an example, like the upper bearing sleeve 6100, the lower bearing sleeve 6200 is constructed of an elastomeric material, e.g., TPE, TPU. The lower bearing sleeve 6200 is arranged between the support portion 6440 and the bearing 6092, e.g., to isolate vibrations, reduce noise, and provide shock absorption, e.g., in the radial direction. Also, the lower bearing sleeve 6200 takes the place of damping or bearing grease, e.g., between the support portion 6440 and the bearing 6092, which facilitates manufacturing.

The lower bearing sleeve 6200 may be permanently (e.g., overmolded) or removably (e.g., interference fit assembly) connected to the support portion 6440 of the intermediate portion 6064.

In the illustrated example, the lower bearing sleeve 6200 and the intermediate portion 6064 comprise an overmolded construction to form a one-piece, integrated component. For example, the intermediate portion 6064 (e.g., along with the overmolded stator assembly 6024) may comprise a first part or base mold and the lower bearing sleeve 6200 may comprise a second part or overmold that is provided (e.g., by overmolding) to the first part. In an example, the intermediate portion 6064 comprises a material (e.g., polycarbonate, polypropylene) that is more rigid than the lower bearing sleeve 6200, e.g., TPE, TPU.

In an example, the lower bearing sleeve 6200 may be overmolded to the intermediate portion 6064 so that the retaining structure 6220 provides an interference fit or mechanical interlock with the intermediate portion 6064. For example, in the illustrated example, the retaining structure 6220 is structured to wrap around a free end of the support wall 6444 to mechanically secure the lower bearing sleeve 6200 to the intermediate portion 6064. In addition, the outer side of the cylindrical or tubular side wall 6210 includes one or more threads or protrusions 6217 adapted to engage within respective grooves provided to the support wall 6444 to secure the lower bearing sleeve 6200 in an operative position. Further, the base wall 6442 of the support portion 6440 includes a plurality of holes 6443 so that, during the overmolding process, the elastomeric material of the lower bearing sleeve 6200 can flow through the holes and form a stake or rivet 6219 onto the support wall 6444 to mechanically secure the lower bearing sleeve 6200 to the intermediate portion 6064. Also, in an example, the elastomeric material of the lower bearing sleeve 6200 may provide interfacing surfaces that bond or stick to the intermediate portion 6064 to enhance the connection with the intermediate portion 6064.

In the illustrated example, the upper end portion 6062, the intermediate portion 6064, and respective upper and lower bearing sleeves 6100, 6200 are structured and arranged to support and align the bearings 6091, 6092, which aligns the rotor 6030 with the axis of the blower 6000. In the illustrated example, the bearings 6091, 6092 are the same size. However, the upper end portion 6062, the intermediate portion 6064, and respective upper and lower bearing sleeves 6100, 6200 may be structured to support and align bearings of different sizes relative to one another.

In an example, a spacer may be provided between each bearing 6091, 6092 and the magnet 6022, e.g., to maintain alignment of the magnet 6022 with the stator assembly 6024.

While the blower example is described as including a three stage design, it should be appreciated that examples of the technology may be applied to other stage designs, e.g., one, two, four, or more stages.

Also, while aspects of the technology are described herein in its application to non-invasive ventilation (NIV) treatment apparatus (e.g., RPT devices), such as CPAP, it is to be understood that aspects of the technology may have application to other fields of application where blowers are used, e.g., in both positive pressure and negative pressure applications.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier 5.6.1 Humidifier Overview

Figure 1:
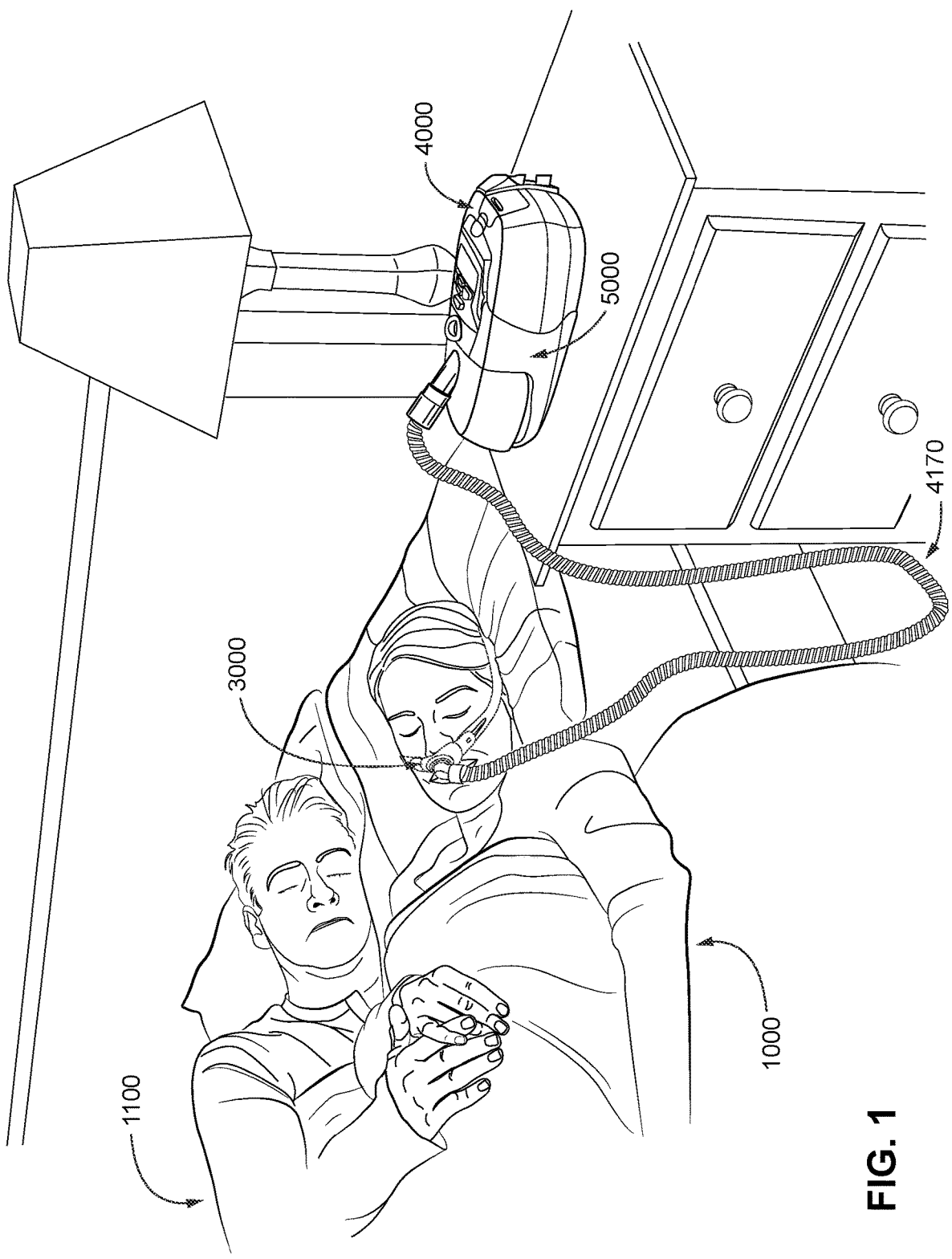

In one form of the present technology there is provided a humidifier 5000 (e.g. as shown in FIG. 1) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

5.7 GLOSSARY

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.3 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 2B to FIG. 2F, which illustrate examples of cross-sections at point p on a surface, and the resulting plane curves. FIGS. 2B to 2F also illustrate an outward normal vector at p. The outward normal vector at p points away from the surface. In some examples we describe the surface from the point of view of an imaginary small person standing upright on the surface.

5.7.3.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 2B (relatively large positive curvature compared to FIG. 2C) and FIG. 2C (relatively small positive curvature compared to FIG. 2C). Such curves are often referred to as concave.

Zero curvature: If the curve at p is a straight line, the curvature will be taken to be zero (if the imaginary small person leaves the point p, they can walk on a level, neither up nor down). See FIG. 2D.

Negative curvature: If the curve at p turns away from the outward normal, the curvature in that direction at that point will be taken to be negative (if the imaginary small person leaves the point p they must walk downhill) See FIG. 2E (relatively small negative curvature compared to FIG. 2F) and FIG. 2F (relatively large negative curvature compared to FIG. 2E). Such curves are often referred to as convex.

5.7.3.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 2B to 2F could be examples of such multiple cross-sections at a particular point.

Principal curvatures and directions: The directions of the normal planes where the curvature of the curve takes its maximum and minimum values are called the principal directions. In the examples of FIG. 2B to FIG. 2F, the maximum curvature occurs in FIG. 2B, and the minimum occurs in FIG. 2F, hence FIG. 2B and FIG. 2F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill)

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.3.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix. A typical human right ear comprises a helix, which is a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule, or alternatively by a left-hand rule.

Osculating plane: The plane containing the unit tangent vector and the unit principal normal vector.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path).

5.7.3.4 Holes

Figure 2G:
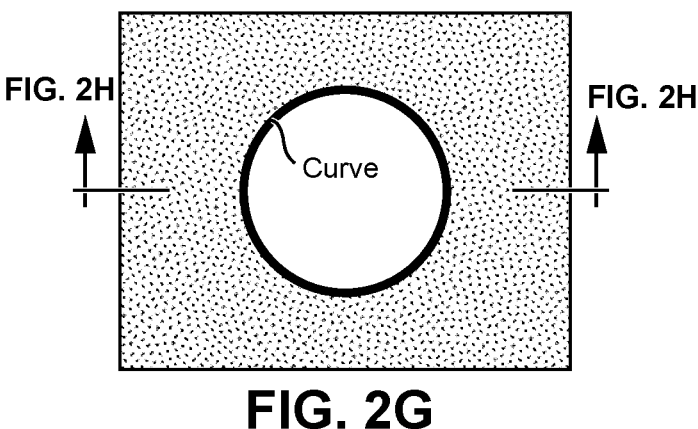
Figure 2H:

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 2G, bounded by a plane curve.

Figure 2I:
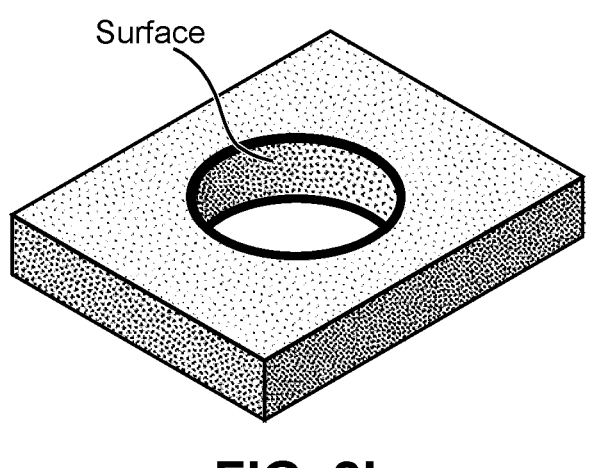

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit. See also the two dimensional hole through the structure shown in FIG. 2I, bounded by a surface as shown.

5.8 OTHER REMARKS

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 REFERENCE SIGNS LIST

| Feature Item | Number |
| --- | --- |
| patient | 1000 |
| bed partner | 1100 |
| patient interface | 3000 |
| seal-forming structure | 3100 |

-continued

| Feature Item | Number |
| --- | --- |
| plenum chamber | 3200 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| lower portion | 4014 |
| panels | 4015 |
| chassis | 4016 |
| handle | 4018 |
| pneumatic block | 4020 |
| filter | 4110 |
| inlet air filter | 4112 |
| air outlet filter | 4114 |
| inlet muffler | 4122 |
| outlet muffler | 4124 |
| pressure generator | 4140 |
| blower | 4142 |
| motor | 4144 |
| air circuit | 4170 |
| supplementary gas | 4180 |
| electrical components | 4200 |
| PCBA | 4202 |
| electrical power supply | 4210 |
| input device | 4220 |
| input devices | 4220 |
| central controller | 4230 |
| transducer | 4270 |
| output device | 4290 |
| humidifier | 5000 |
| blower | 6000 |
| inlet cover | 6010 |
| blower inlet | 6015 |
| motor | 6020 |
| magnet | 6022 |
| stator assembly | 6024 |
| lamination stack | 6026 |
| windings | 6028 |
| rotor | 6030 |
| first impeller | 6041 |
| second impeller | 6041 |
| third impeller | 6043 |
| first stationary component | 6050 |
| stator vanes | 6055 |
| second stationary component | 6060 |
| upper end portion | 6062 |
| intermediate portion | 6064 |
| stator vanes | 6065 |
| lower end portion | 6066 |
| stator vanes | 6067 |
| tube portion | 6068 |
| stakes | 6069 |
| third stationary component | 6080 |
| stator vanes | 6085 |
| blower outlet | 6088 |
| upper bearing | 6091 |
| lower bearing | 6092 |
| spring | 6095 |
| upper bearing sleeve | 6100 |
| cylindrical side wall | 6110 |
| ribs | 6115 |
| retaining structure | 6120 |
| lower bearing sleeve | 6200 |
| cylindrical side wall | 6210 |
| ribs | 6215 |
| threads | 6217 |
| rivet | 6219 |
| retaining structure | 6220 |
| cylindrical side wall | 6310 |
| end wall | 6320 |
| opening | 6330 |
| support portion | 6340 |
| base wall | 6342 |
| hole | 6343 |
| support wall | 6344 |

-continued

| Feature Item | Number |
| --- | --- |
| side wall | 6345 |
| side wall | 6346 |
| channel | 6348 |
| intermediate connection portion | 6350 |
| openings | 6352 |
| cylindrical side wall | 6410 |
| end wall | 6420 |
| opening | 6430 |
| support portion | 6440 |
| base wall | 6442 |
| hole | 6443 |
| support wall | 6444 |

The invention claimed is:

1. A blower, comprising:

a rotor;

a motor configured to drive the rotor;

at least one bearing configured to rotatably support the rotor;

a stationary component; and a bearing sleeve provided to the stationary component, the bearing sleeve configured and arranged to support and retain the bearing to the stationary component, wherein the bearing sleeve comprises an elastomeric material, wherein the bearing sleeve comprises one or more bumps or ribs configured to engage along an outer race of the bearing, wherein the bearing sleeve comprises an overmolded connection to the stationary component, wherein the bearing sleeve comprises a cylindrical side wall and a retaining structure configured and arranged to form a mechanical connection to the stationary component, wherein the one or more bumps or ribs are provided to an inner side of the cylindrical side wall, wherein the retaining structure is configured to wrap around a support wall of the stationary component, wherein an outer side of the cylindrical side wall includes threads configured to engage within respective grooves provided to the support wall of the stationary component to secure the bearing sleeve in an operative position, and wherein the retaining structure forms a separate and distinct structure from the threads.

2. The blower according to claim 1, wherein the elastomeric material comprises TPE.

3. The blower according to claim 1, wherein the stationary component comprises stator vanes.

4. The blower according to claim 1, wherein the bearing sleeve comprises at least two bumps or ribs arranged between the stationary component and the bearing to isolate vibrations, reduce noise, and provide shock absorption.

5. The blower according to claim 1, wherein the bearing sleeve protrudes through one or more holes provided to the stationary component to form a stake or rivet onto the stationary component.

6. The blower according to claim 1, further comprising a biasing element configured to provide a pre-load force to the at least one bearing, wherein the bearing sleeve is configured to protrude past the bearing and provide a space for enclosing and positioning the biasing element.

7. The blower according to claim 6, wherein the biasing element comprises a spring.

8. The blower according to claim 6, wherein the biasing element is configured to provide the pre-load force to an inner race of the bearing.

9. A CPAP system for providing gas at positive pressure for respiratory therapy to a patient, the CPAP system comprising:

an RPT device configured to supply a flow of gas at a therapeutic pressure, the RPT device comprising the blower according to claim 1;

a patient interface; and an air delivery conduit configured to pass the flow of gas at the therapeutic pressure from the RPT device to the patient interface.

* * * * *